United States Patent [19]

Baasner et al.

[11] Patent Number: 5,019,654
[45] Date of Patent: May 28, 1991

[54] FLUORINATED TERTIARY BUTYLAMINES

[75] Inventors: Bernd Baasner; Hermann Hagemann, both of Leverkusen; Michael Schwamborn, Cologne, all of Fed. Rep. of Germany

[73] Assignee: Bayer Aktiengesellschaft, Leverkusen, Fed. Rep. of Germany

[21] Appl. No.: 27,705

[22] Filed: Mar. 19, 1987

[30] Foreign Application Priority Data

Apr. 4, 1986 [DE] Fed. Rep. of Germany ....... 3611195

[51] Int. Cl.$^5$ ............................................ C07C 211/07
[52] U.S. Cl. ..................................... 564/510; 564/463
[58] Field of Search .......................................... 564/510

[56] References Cited

U.S. PATENT DOCUMENTS 4,549,994 10/1985 Hagemann et al. ................. 560/161
4,609,648 9/1986 Schwamborn et al. ............. 514/465

FOREIGN PATENT DOCUMENTS 0132729 2/1985 European Pat. Off. .
3326873 2/1985 Fed. Rep. of Germany .
3326874 2/1985 Fed. Rep. of Germany .
3326875 2/1985 Fed. Rep. of Germany .

OTHER PUBLICATIONS

Houben-Weyl, Methoden der Organischem Chemie (Methods of Organic Chemistry), vol. IX/1, 862-872 (1957).
Houben-Weyl, Methoden der Orgainischen Chemie (Methods of Organic Chemistry), vol. XI/1, pp. 854-862 (1957).
Methoden der Organischen Chemie, Houben-Weyl, vol. IX, 1955, pp. 867-872, Thieme-Verlag Stuttgart.
Synthesis, pp. 551-553, (1972).

Primary Examiner—Glennon H. Hollrah
Assistant Examiner—Susan P. Treanor
Attorney, Agent, or Firm—Sprung Horn Kramer & Woods

[57] ABSTRACT

New fluorinated tertiary butylamines of the formula

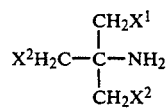

are prepared from halogenated pivalic acid halides by a reaction sequence which comprises preparing the fluorinated pivalic acid and decomposition of the azide to the corresponding isocyanate. The isocyanate can be converted to the fluorinated tertiary butylamine acid addition salt by acid hydrolysis or directly to the amine by treatment with base. In addition, the present amines can be prepared by reaction of a pivalic acid amide with hypochlorite. The new butylamines can be used in the preparation of benzoic acid amides having insecticidal action.

4 Claims, No Drawings

FLUORINATED TERTIARY BUTYLAMINES

The present application relates to new fluorinated tertiary butylamines and several processes for their preparation.

These new fluorinated tertiary butylamines are of the formula (I)

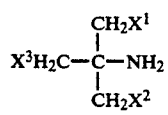

in which the radicals $X^1$ to $X^3$ can be identical or different and represent hydrogen or fluorine, but at least one of the radicals $X^1$ to $X^3$ must represent fluorine.

The fluorinated tertiary butylamines of the formula (I)

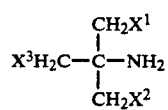

in which the radicals $X^1$ to $X^3$ can be identical or different and represent hydrogen or fluorine and at least one of the radicals $X^1$ to $X^3$ represents fluorine, are obtained by a procedure in which, in process variant A) (a) the halogenated pivalic acid halides of the general formula (II)

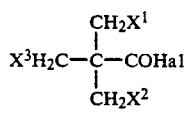

in which $X^1$ to $X^3$ have the abovementioned meaning and

Hal represents fluorine or chlorine, are converted with a reagent which donates azido groups into the fluorinated pivalic acid azides of the general formula (III)

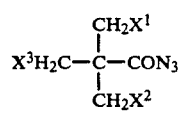

in which
$X^1$ to $X^3$ have the abovementioned meaning, and
(b) the optionally isolated compounds of the general formula (III) are decomposed by means of heat to give the fluorinated isocyanates of the general formula (IV)

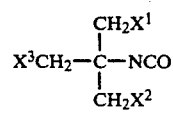

in which
$X^1$ to $X^3$ have the abovementioned meaning, and
(c) the optionally isolated compounds of the general formula (IV) are converted by acid hydrolysis into the fluorinated tertiary butylamine acid addition salts of the general formula (V)

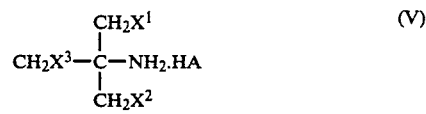

in which
$X^1$ to $X^3$ have the abovementioned meaning and
A represents the monovalent radical of an acid, and
(d) the optionally isolated compounds of the general formula (V) are converted by treatment with a base into the fluorinated tertiary butylamines of the general formula (I), or, in process variant B), the compounds of the formula (IV)

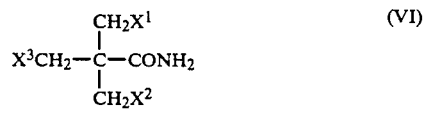

are converted directly by alkaline hydrolysis into the fluorinated tertiary butylamines of the general formula (I), or, in process variant C), pivalic acid amides of the general formula (VI)

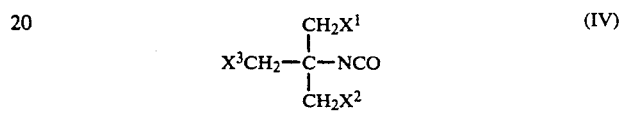

in which
$X^1$ to $X^3$ have the abovementioned meaning, are converted by reaction with hypohalite into the fluorinated tertiary butylamines of the general formula (I).

The new compounds of the general formula (I) are useful as intermediates for syntheses in organic chemistry, for example in the fields of dyestuffs, pharmaceuticals, plant protection agents, plastics and rubber auxiliaries.

The new compounds of the formula (I) are particularly suitable for the preparation of new benzoic acid amides which have an insecticidal action.

The following synthesis may be given here as an example:

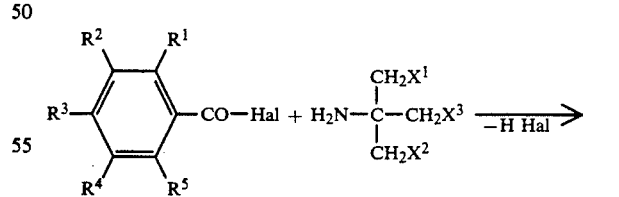

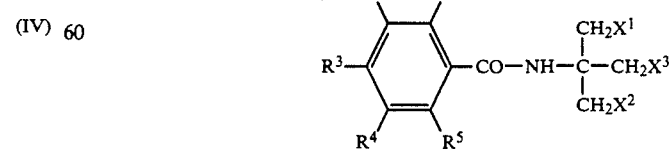

wherein
$X^1$ to $X^3$ have the abovementioned meaning and the radicals $R^1$, $R^2$, $R^3$, $R^4$ and $R^5$ are identical or different and represent hydrogen, halogen, nitro, alkyl, halogenoalkyl, halogenoalkoxy or halogenoalkylthio.

The following compounds of the general formula (I) are possible: 2-fluoro-1,1-dimethyl-ethylamine, 2-fluoro-1-(monofluoromethyl)-1-methyl-ethylamine and 2-fluoro-1,1-bis -(monofluoromethyl)-ethylamine.

If monofluoropivaloyl chloride is used as the starting substance in process variant A), the reaction sequence (a) to (d) can be represented as follows:

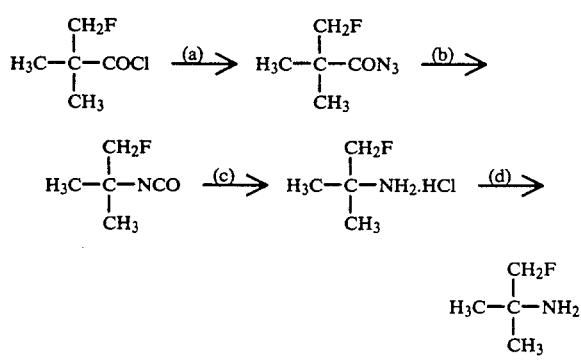

If 2-fluoro-1,1-dimethylethyl isocyanate is used as the starting compound in process variant B) and hydrolysis is carried out with aqueous sodium hydroxide solution, the reaction can be represented as follows:

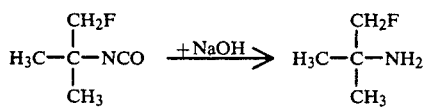

If monofluoropivaloylamide is used as the starting substance in process variant C) and the reaction in the context of a Hofmann degradation is carried out with hypohalite, the reaction can be represented as follows:

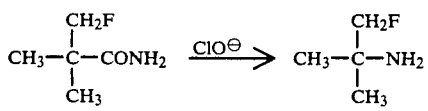

As regards preparation variant A):

The compounds of the general formulae (I) to (V) obtained in the individual process stages (a) to (d) can either be isolated by customary methods or further processed directly, without isolation, in the next stage The fluorinated pivalic acid halides of the general formula (I) to be employed as starting substances are known from DE-OS (German Published Specification) 3,326,875. DE-OS (German Published Specification) 3,326,873 discloses that 2-fluoro-1-(monofluoromethyl)-1-methyl-propionyl fluoride is converted into the corresponding azide, this is converted into 2-fluoro-1-(monofluoromethyl)-1-methyl isocyanate, without intermediate isolation, and, finally, this can be reacted with 2-propine alcohol, without intermediate isolation, to give 0-2-propinyl N-(1,1-bisfluoromethyl-ethyl)-carbamate, which can be used as an agent for combating pests.

The reaction stages (a) to (d) can be carried out by the customary methods of organic chemistry.

In reaction stage (a), the fluorinated pivalic acid halides of the general formula (II) are converted with a reagent which donates azide groups into the azides of the general formula (III) (see, for example, Houben-Weyl, Methoden der organischen Chemie (Methods of Organic Chemistry), Volume IX/1, 862 - 872 (1957)). For this, the fluorinated pivalic acid halides are dissolved, for example in acetone, and reacted with an approximately molar amount of sodium azide (in aqueous solution) at about 0° C. to about +20° C. The mixture is then extracted with an inert organic solvent, such as, for example, toluene, and the organic phase is separated off and dried. The azides can be separated off from this solution by distillation.

An advantageous process comprises converting the fluorinated pivalic acid halides of the general formula (II) with trimethylsilyl azide into the azide of the general formula (III) by the process described in Synthesis 1972, 551-553. The azide can then also be isolated by distillation.

The azides of the general formula (II) thus obtained can be employed for the further conversion into the isocyanate of the general formula (IV) in their pure form, but preferably in the form of their dilute solutions, such as are obtained in the preceding step. The conversion of the azides into the isocyanates is likewise carried out by known processes (see, for example, Houben-Weyl, Methoden der organischen Chemie (Methods of Organic Chemistry), Volume XI/1, 862–872 (1957)), by heating the azide in an inert organic solvent, such as, for example, benzene or toluene, until the evolution of nitrogen has ended. The isocyanate can then be obtained in a pure form by distillation.

The isocyanate of the general formula (IV) thus obtained is converted into the amine acid addition salt of the general formula (V) in the subsequent reaction stage. In this, the isocyanate of the general formula (IV) is preferably hydrolyzed in aqueous hydrochloric acid of any desired concentration.

This hydrolysis can be carried out in the aqueous acid or in the presence of an inert organic solvent at temperatures between 0° and +100° C. The reaction time is between 0.5 and 18 hours. After the volatile constituents have been distilled off under normal pressure or reduced pressure, the pure amine hydrochloride of the general formula (V) remains as the residue. The free amine of the general formula (I) can be obtained from this by treatment with an alkali for neutralization of the hydrochloric acid from the hydrochloride. The amine is obtained in pure form by distillation from this crude mixture. Instead of hydrochloric acid, any other suitable mineral acid, such as, for example, sulphuric acid, can also be used for the hydrolysis. However, it is also possible for the amine of the general formula (I) to be extracted from this crude mixture with an inert organic solvent and for the amine to be isolated from this extract by distillation. It is furthermore possible for the free amine of the general formula (I) to be isolated from the neutralized or alkalized crude mixture of the isocyanate hydrolysis by distillation or extraction. It is moreover possible for the amine (I) to be liberated from the isocyanates of the general formula (IV) by basic hydrolysis with alkali metal hydroxide solutions and to be isolated in the pure form from this crude mixture by distillation or extraction with subsequent distillation by the methods already described.

It is moreover possible for the pivalic acid amides of the general formula (VI)

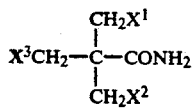

$$\begin{array}{c} \text{CH}_2\text{X}^1 \\ | \\ \text{X}^3\text{CH}_2-\text{C}-\text{CONH}_2 \\ | \\ \text{CH}_2\text{X}^2 \end{array} \quad \text{(VI)}$$

in which $X^1$ to $X^3$ have the abovementioned meaning, to be converted into the tertiary butylamines of the general formula (I) by Hofmann degradation with hypohalite in accordance with known processes (see, for example, Houben-Weyl, Methoden der organischen Chemie (Methods of Organic Chemistry), Volume XI/1, pages 854–862 (1957)).

The compounds of the general formula (VI) are likewise known from DE-OS (German Published Specification) 3,326,874. They are prepared by reaction of the carboxylic acid halides of the general formula (II) with ammonia.

EXAMPLES

Example 1

2-Fluoro-1,1-dimethyl-ethyl isocyanate from monofluoropivaloyl chloride with trimethylsilyl azide 69.5 g (0.5 mol) of monofluoropivaloyl chloride are added dropwise to a solution of 70 g of trimethylsilyl azide in 300 ml of toluene in the course of about 10 minutes. The mixture is stirred for 30 minutes, during which the temperature rises to 45° C. and evolution of gas starts. The temperature is then increased slowly (up to 90° C. in the course of about 5 hours) and the mixture is stirred until the evolution of gas has ended. The progress of the reaction is monitored by IR spectroscopy (decrease in the azide band at 2130 cm$^1$). The isocyanate is distilled off from this reaction solution. 52.1 g (89% of theory) of 2-fluoro-1,1-dimethyl-ethyl isocyanate 5 of boiling point 98–100° C. (under normal pressure) are obtained.

Example 2

2-Fluoro-1,1-dimethyl-ethyl isocyanate from monofluoropivaloyl fluoride with sodium azide A solution of 6.6 g of sodium azide in 20 ml of water is added dropwise to 12.2 g (0.1 mol) of monofluoropivaloyl fluoride in 200 ml of acetone at 0° C. to +5° C., while cooling with an ice-bath. The mixture is subsequently stirred for 1 hour, 300 ml of ice-water are added and the mixture is extracted three times with 100 ml of toluene each time. The organic phase is washed once with 200 ml of water and dried with magnesium sulphate. The azide solution thus prepared is then heated up slowly (to 90° C. in the course of about 3 hours) and subsequently stirred until the evolution of gas has ended (monitoring of the reaction by IR spectroscopy as described in Example 1). The isocyanate can be distilled off from this solution. 9.5 g (81% of theory) of 2-fluoro-1,1-dimethylethyl isocyanate of boiling point 99–100° C. (under normal pressure) are obtained.

Example 3

2-Fluoro-1,1-dimethyl-ethyl isocyanate from monofluoropivaloyl fluoride with trimethylsilyl azide 61 g (0.5 mol) of monofluoropivaloyl fluoride are reacted with trimethylsilyl azide analogously to Example 1. When the evolution of gas has ended, solution is distilled. 53.8 g (92% of theory) of 2-fluoro-1,1-dimethyl-ethyl isocyanate of boiling point 96–99° C. (under normal pressure) are obtained.

Example 4

2-Fluoro-1,1-dimethyl-ethyl isocyanate from monofluoropivaloyl chloride with sodium azide 13.9 g (0.1 mol) of monofluoropivaloyl chloride are reacted with sodium azide analogously to Example 2. 9 g (77% of theory) of 2-fluoro-1,1-dimethyl-ethyl isocyanate of boiling point 100–101° C. (under normal pressure) are obtained.

Example 5

2-Fluoro-1-(monofluoromethyl)-1-methyl-ethyl isocyanate from 3-fluoro-2-(monofluoromethyl)-2-methylpropionyl fluoride 70 g (0.5 mol) of 3-fluoro-2-(monofluoromethyl)-2-methyl-propionyl fluoride are reacted with 70 g of trimethylsilyl azide analogously to Example 3, but in benzene as the solvent. The reaction mixture is heated under reflux until the evolution of gas has ended. The volatile constituents and then the isocyanate are subsequently distilled off over a short packed column. 56 g (83%) of 2-fluoro-1-(monofluoromethyl)-1-methyl-ethyl isocyanate of boiling point 122–124° C. (under normal pressure) are obtained.

Example 6

2-Fluoro-1,1-bis-(monofluoromethyl)-ethyl isocyanate from 3-fluoro-2,2-bis-(monofluoromethyl)-propionyl chloride with trimethylsilyl azide 87.25 g (0.5 mol) of 3-fluoro-2,2-bis-(monofluoromethyl)-propionyl chloride are reacted with 70 g of trimethylsilyl azide analogously to Example 1, but in benzene as the solvent. The reaction mixture is heated under reflux until the evolution of gas has ended. The volatile constituents and then the isocyanate are subsequently distilled off over a short packed column. 65.4 g (85.5% of theory) of 2-fluoro-1,1-bis-(monofluoromethyl)-ethyl isocyanate of boiling point 143–146° C. (under normal pressure) are obtained.

Example 7

2-Fluoro-1,1-(dimethyl)-ethylamine hydrochloride 58.5 g (0.5 mol) of 2-fluoro-1,1-dimethyl-ethyl isocyanate, such as can be obtained according to Examples 1 to 4, are added dropwise, in 300 ml of toluene, to 400 ml of concentrated hydrochloric acid in the course of about 30 minutes (evolution of gas). The mixture is then stirred at 60° C. until the evolution of gas has ended (about one hour). After the volatile constituents have been distilled off, the product 2-fluoro-1,1-(dimethyl)-ethylamine hydrochloride is obtained Yield 60.6 g (95% of theory). Melting point 248° C. (with decomposition).

Example 8

2-Fluoro-1,1-dimethyl-ethylamine 60 g of 45% strength aqueous NaOH are added dropwise to 63.75 g (0.5 mol) of 2-fluoro-1,1-(dimethyl)-ethylamine hydrochloride from Example 7 at an oil bath temperature of 100° C. At the same time, the amine liberated is distilled off. After drying over magnesium sulphate, the product is redistilled. 2-Fluoro-1,1-dimethyl-ethylamine is obtained as the product. Yield 41.4 g (91% of theory). Boiling point: 82–84° C. (under normal pressure), $n_D^{20}$:1.4042.

Example 9

2-Fluoro-1-(monofluoromethyl)-1-methyl-ethylamine hydrochloride 62.5 g (86% of theory) of 2-fluoro-1-(monofluoromethyl)-1-methyl-ethylamine hydrochloride are obtained analogously to Example 7 from 67.5 g (0.5 mol) of 2-fluoro-1-(monofluoromethyl)-1-methyl isocyanate, which is prepared according to Example 5. Melting point 214° C. (with decomposition).

Example 10

2-Fluoro-1-(monofluoromethyl)-1-ethylamine 50.7 g (93% of theory) of 2-fluoro-1-(monofluoromethyl)-1-methyl-ethylamine of boiling point 91–92° C. (under normal pressure) and $n_D^{20}$:1.3892 are obtained analogously to Example 8 from 72.25 g (0.5 mol) of 2-fluoro-1-(monofluoromethyl-1)-1-methyl-ethylamine hydrochloride from Example 9.

Example 11

2-Fluoro-1,1-bis-(monofluoromethyl)-ethylamine hydrochloride 75 g (92% of theory) of 2-fluoro-1,1-bis-(monofluoromethyl)-ethylamine hydrochloride are obtained analogously to Example 7 from 76.5 g (0.5 mol) of 2-fluoro-1,1-bis-(monofluoromethyl) isocyanate, which is prepared according to Example 6. Melting point 220° C. (with decomposition).

Example 12

2-Fluoro-1,1-bis-(monofluoromethyl)-ethylamine 54.6 g (86% of theory) of 2-fluoro-1,1-bis-(monofluoromethyl)-ethylamine of boiling point 120–122° C. (under normal pressure) and $n_D^{20}$:1.3813 are obtained analogously to Example 8 from 81.75 g (0.5 mol) of 2-fluoro-1,1-bis-(monofluoromethyl)-ethylamine hydrochloride from Example 11.

What is claimed is:

1. A fluorinated tertiary butylamine of the formula

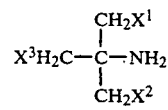

in which the radicals $X^1$ to $X^3$ each independently represent hydrogen or fluorine, but at least one of the radicals $X^1$ to $X^3$ must represent fluorine.

2. A fluorinated butylamine according to claim 1, wherein said butylamine is 2-fluoro-1,1-dimethylethylamine.

3. A fluorinated butylamine according to claim 1, wherein said butylamine is 2-fluoro-1-(monofluoromethyl)-1-methyl-ethylamine.

4. A fluorinated butylamine according to claim 1, wherein said butylamine is 2-fluoro-1,1-bis(monofluoromethyl)-ethylamine.

* * * * *